United States Patent
Turnbull et al.

(10) Patent No.: US 7,794,412 B2
(45) Date of Patent: Sep. 14, 2010

(54) DEVICE FOR APPLYING AND GAUGING CRICOID PRESSURE

(75) Inventors: Christopher J. Turnbull, Sarasota, FL (US); Richard L. Globensky, Taylors Falls, MN (US)

(73) Assignee: T Medical, Inc., Owatonna, MN (US)

( * ) Notice: Subject to any disclaimer, the term of this patent is extended or adjusted under 35 U.S.C. 154(b) by 853 days.

(21) Appl. No.: 11/127,383

(22) Filed: May 12, 2005

(65) Prior Publication Data

US 2006/0258960 A1 Nov. 16, 2006

(51) Int. Cl.
 *A61B 5/103* (2006.01)
 *A61B 5/117* (2006.01)
(52) U.S. Cl. ..................................... 600/587
(58) Field of Classification Search ................. 128/207; 600/587
See application file for complete search history.

(56) References Cited

U.S. PATENT DOCUMENTS

| | | | | |
|---|---|---|---|---|
| 2,799,270 | A * | 7/1957 | Rodbard | 600/491 |
| 5,483,974 | A | 1/1996 | Crangle | 128/774 |
| 6,119,695 | A | 9/2000 | Augustine et al. | 128/207.15 |
| 6,422,873 | B1 * | 7/2002 | Abdelatti | 434/262 |
| 2002/0091039 | A1 * | 7/2002 | Reinbold et al. | 482/1 |

FOREIGN PATENT DOCUMENTS

| | | |
|---|---|---|
| EP | 1043040 A2 | 10/2000 |
| WO | WO 02/37453 A1 | 5/2002 |

OTHER PUBLICATIONS

Lawes, et al., "The cricoid yoke—a device for providing consistent and reproducible cricoid pressure", *Br. J. Anaesth.* (1986), 58, 925-931.
Vanner, et al., "Upper oesophageal sphincter pressure and the effect of cricoid pressure", aesthesia, 1992, vol. 47, pp. 95-100.
Koziol, et al., "Assessing the force generated with application of cricoid pressure", AORN Journal, Dec. 2000, vol. 72, No. 6.

\* cited by examiner

*Primary Examiner*—Max Hindenburg
*Assistant Examiner*—Sean P Dougherty
(74) *Attorney, Agent, or Firm*—Thomas J. Nikolai; Nikolai & Mersereau, P.A.

(57) ABSTRACT

The invention is a device for objectively applying cricoid pressure. A healthcare provider, using a locator on the face of the device, aligns the yoke with the patient's cricoid cartilage. While the healthcare provider applies force to the cricoid cartilage, a stem portion affixed to the yoke and projecting from the first end is coupled to a force sensor in the housing. The electrical signal from the force sensor is translated to a digital value by an analog-to-digital converter. The digital signal is then compared by a microprocessor to pre-established threshold values, which is reflected in a visual, auditory, or tactile signal to gauge the force being applied to the patient's cricoid cartilage.

21 Claims, 3 Drawing Sheets

DEVICE FOR APPLYING AND GAUGING CRICOID PRESSURE

BACKGROUND OF THE INVENTION

1. Field of the Invention

This invention relates to a medical device which assists in the application of cricoid pressure (CP) during medical procedures such as intubation of the trachea or other airway management procedures where there is a concern of aspiration of gastric contents into the lungs or insufflation of air into the stomach causing gastric distension.

2. Discussion of the Prior Art

Doctors, nurses, paramedics, among others, frequently perform bag/mask ventilation or intubation of the trachea with an endotracheal tube. Such medical personnel frequently must secure the airway employing a rapid sequence intubation technique utilizing general anesthesia medications. In an emergency situation, the medical personnel will not know if the patient has a full-stomach. Patients who require advanced airway management services including bag/mask ventilation and rapid sequence intubation are at risk for aspiration of their gastric contents. Aspiration of gastric contents is associated with morbidity and potential mortality.

The application of pressure to the cricoid cartilage, also known as the Sellick maneuver, is the standard of care in the anesthesia community. The application of cricoid pressure has traditionally been accomplished manually, where a trained health care provider will use his or her fingers to apply the pressure. When indicated, before the induction of general anesthesia, the cricoid cartilage is palpated and held between the assistant's thumb and the second finger. The assistant's index finger is then used to apply pressure on the cricoid cartilage. As induction of general anesthesia is commenced, pressure is exerted on the cricoid cartilage, such that the cricoid cartilage is pushed up against the cervical vertebrae. The esophagus is thus occluded in an effort to prevent aspiration of gastric contents and insufflation of air into the stomach during positive pressure bag/mask ventilation.

Clinical research has determined that approximately 20 to 40 newtons of cricoid pressure is necessary to achieve esophageal occlusion, which effectively prevents regurgitation of gastroesophageal contents into the lungs of the patient. In terms of Newton's (N), the recommended force to be exerted before loss of consciousness is 20 N, or approximately 2 kg of force. The force is then increased to between 30 to 40 N, or 3 kg to 4 kg of force for an unconscious person.

Too much or too little force may put the patient at risk. Too much force may damage the trachea or other surrounding anatomical structures or may result in inadequate patient ventilation. Too little force on the cricoid cartilage undermines the efficacy of the procedure by failing to occlude the esophagus to prevent aspiration of gastric contents. Because of the importance of the amount of cricoid pressure, the person applying the pressure must know how to do so properly. Even a trained doctor, nurse, or paramedic, however, cannot objectively apply and maintain the proper pressure without some method of determining the cricoid pressure being applied.

An instrument designed to inform the user of the force being applied to the cricoid cartilage needs to be easy to place precisely, must provide accurate indications when the necessary force has been obtained, should not interfere with ventilation or intubation, and should cause very little trauma to the patient.

As a method of training healthcare providers in applying cricoid pressure, Carol A. Koziol, RN, et al, in *AORN Journal* Vol. 27, No. 6, (2000) suggests placing a model of a cricoid cartilage on a scale, and then measuring the force so that the healthcare provider can get a feel for what their actual performance should be in the perioperative setting. However, this method is only a training method, and does not provide an accurate indication of when the necessary force is being applied to an actual patient.

U.S. Pat. No. 5,483,974 granted on Jan. 16, 1996 to Richard Crangle entitled "Device To Apply, Hold, and Measure Cricoid Pressure During Entotracheal Intubation or Cricothyroidotomies, or Other Medical Airway Procedures" shows an arrangement where a contact cushion is disposed directly on the front of the neck, and held in place using an adjustable strap. Once the Crangle device is attached to the neck of the patient, the healthcare provider then applies pressure to the entire apparatus using his or her hands. When the device is employed, the surface of the device engages a bladder, creating pressure against the cricoid cartilage and the pressure is translated to a release valve and a dial indicator. If the force applied exceeds the recommended number of Newtons, a release valve will automatically depressurize the compressible bladder.

Crangle's approach, however, is both cumbersome, and difficult to use. First, the manufacture of such a device, which includes a bladder of suitable size, with a pressure gauge, and a release valve will necessarily result in a bulky device that is awkward for both the healthcare provider and the patient. Second, the device is not simple to use from the perspective of the healthcare provider. It is a two-step process of first attaching the device to the patient's neck, and then applying necessary force. In an emergency situation, the healthcare provider will be wasting precious time following these two steps, rather than using a device that requires only the step of applying force to the cricoid cartilage. Finally, from the perspective of the patient who is still conscious, having such a cumbersome device attached to his or her neck might be at best awkward, and at worst extremely uncomfortable, and traumatic.

European Patent Application, EP 1 043 040 A2, entitled "A Device For Use In The Application Of Cricoid Pressure (Force) and/or In Training For Such Application" discloses a plastic cylinder, a piston with a seal and an aneroid pressure gauge connected to the nozzle of the cylinder. The healthcare provider places the tip of the piston on the cricoid cartilage of the patient and then presses down on two wings on the cylinder with his index finger and thumb. The air pressure near the top of the cylinder is then measured indicating the amount of force being applied to the patient's cricoid.

This approach will, over time, become dangerously inaccurate. The seal necessary to capture the air pressure will, over time, begin to break down leading either to an inaccurate or useless reading. Attempts to sterilize the device will rapidly deteriorate the seal, also leading to inaccurate and useless readings. Furthermore, this device is not ergonomically sound from the perspective of the healthcare provider. In some instances, cricoid pressure must be maintained for over 30 minutes. In that time, the healthcare provider's fingers may become sore from the continuous application of pressure.

E. G. Lawes, et al, in the *British Journal of Anaesthesia* vol. 58 (1986) discloses a device which measures cricoid pressure by the closing of a circuit. The three essential elements of the device include a foam contact cushion, which is used to apply a force to the cricoid cartilage, a Perspex platform carrying a simple circuit, and stainless steel flexible wings. The healthcare provider grips the device with both hands with upturned end of the wings using his forefingers and thumbs. Once the contact cushion is applied to the patient's neck, the healthcare provider then presses down simultaneously on both wings. When a force of 44 N has been applied, a circuit on the Perspex platform is activated by means of a contact breaker.

The Lawes device is deficient in several ways. First, by requiring the healthcare provider to use both hands to apply pressure to the cricoid, she or he is not free to provide the necessary support to the back of the patient's neck. Without this support, the neck may flex forward and interfere with airway management. Second, the device only is designed to alert the user when a pressure of 44 N has been achieved. As previously mentioned, 44 N is only the appropriate limit on cricoid pressure for an unconscious patient. For a patient who is still conscious, the device does not alert the user when pressure of 20 N has been achieved.

SUMMARY OF INVENTION

A primary object of this invention is to provide a hand held device used with a single hand for assisting the healthcare practioner in measuring and applying pressure to the cricoid cartilage during airway management when there is a concern of aspiration of gastric contents into the lungs or insufflation of air into the stomach.

An additional object of this invention is to provide a single-handed use device for assisting the healthcare practioner in properly locating the cricoid cartilage when the cricothyroid membrane is identifiable.

Another object of this invention is to provide a hand held device for measuring and applying force to the cricoid cartilage that is ergonomically designed so that prolonged comfortable use may take place with little discomfort to the person using the gauge.

A further object of this invention is to provide a hand-held device of measuring and applying pressure to the cricoid cartilage that is ideally sized to interface with the cricoid cartilage of most people.

An additional object of this invention is to provide a hand held device for measuring and applying pressure to the cricoid cartilage that can be held in one hand and which operates accurately for prolonged uses up to and perhaps exceeding one hour.

An additional object of this invention is to provide a hand held device for objectively measuring and applying pressure to the cricoid cartilage where an LED display indicates when pressure is about 20 to 40 Newtons of force and when pressure is greater than 40 Newtons of force.

These and other objects are achieved by providing an apparatus for indicating when a predetermined force is applied to the cricoid cartilage of a patient. The apparatus contains a supply of electrical energy, which powers an indicator device to alert the user as to the amount of pressure being applied to the patient's cricoid cartilage. Forces applied by the healthcare provider to the cricoid cartilage are gauged by the device's force-sensing technology which then produces an electric signal. The electrical signal from the force sensing-technology is translated to a digital value by an analog-to-digital converter. The digital signal is then compared by a microprocessor to pre-established threshold values, which is reflected in a visual, auditory, or tactile signal to gauge the force being applied to the patient's cricoid cartilage.

BRIEF DESCRIPTION OF THE DRAWINGS

The foregoing features, objects and advantages of the invention will become apparent to those skilled in the art from the following detailed description from the preferred embodiment, especially when considered in conjunction with the accompanying drawings in which like numerals in the several views refer to corresponding parts.

DETAILED DESCRIPTION OF INVENTION

Figure 1:
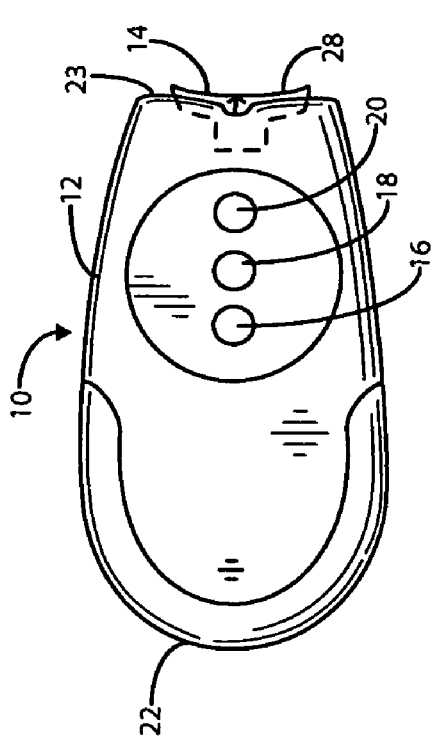
FIG. 1 shows a top view of the cricoid pressure device of the present invention.

Referring first to FIG. 1, the preferred embodiment of the present invention is seen to comprise a device for measuring the amount of force applied to the cricoid cartilage. The device 10 generally includes housing 12, a yoke member 14, and indicators 16, 18, and 20. The housing 12 is generally an elongated member that extends from an ergonomically rounded end 22 to a front end 23. The ergonomically rounded end 22 is shaped such that the user can grasp the device into the palm of his/her hand, by fitting the rounded end 22 comfortably against the web of skin (Thenar eminence) between the user's thumb and the index finger. The housing 12 is preferably a molded plastic, but may be formed from metal as well.

On the top surface of housing 12 are indicators 16, 18, and 20. These indicators are preferably each different colored LEDs for communicating the amount of pressure being applied on a patient's neck by the device 10.

Partially protruding from end 23 is a yoke member 14. Yoke 14 is generally an arcuate member supported by a rod that is internally mounted within the housing 12. The curved outer surface 28 of the yoke can be seen. This curved outer surface 28 is the surface which is pressed against a patient's neck when the invention is in use.

Additionally, an electrical energy supply (not shown) is contained in the housing to activate the indicators 16, 18, and 20.

Figure 2:
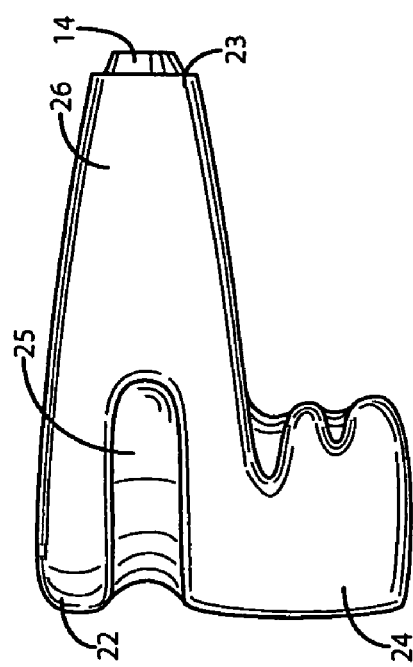
FIG. 2 shows a side view of the cricoid pressure device.

FIG. 2 discloses a side view of the cricoid pressure device 10. Generally, housing 12 has an upper elongated portion 26 and a base protrusion 24. Protrusion 24 includes a number of folds on its interior side and a smoothly rounded outer surface which extends adjacent to and below ergonomically rounded end 22. A recessed groove 25 wraps around the ergonomically rounded end 22 and the back third of the housing 12. The recessed groove 25 is wide enough so that the web of skin (Thenar eminence) between a user's thumb and the index finger can fit comfortably within this recessed grove 25. Upper protrusion 26 comprises the portion of the housing that extends away from rounded end 22. Generally, the upper protrusion 26 narrows slightly as it approaches front end 23 and yoke 14.

Figure 3:
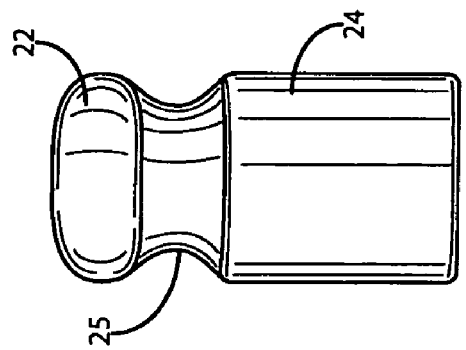
FIG. 3 shows a rear view of the cricoid pressure device.

FIG. 3 shows a rear view of the cricoid pressure device. The shape of recessed groove 25 is seen, as well as the contours of rounded end 22 as it merges with base 24.

Figure 4:
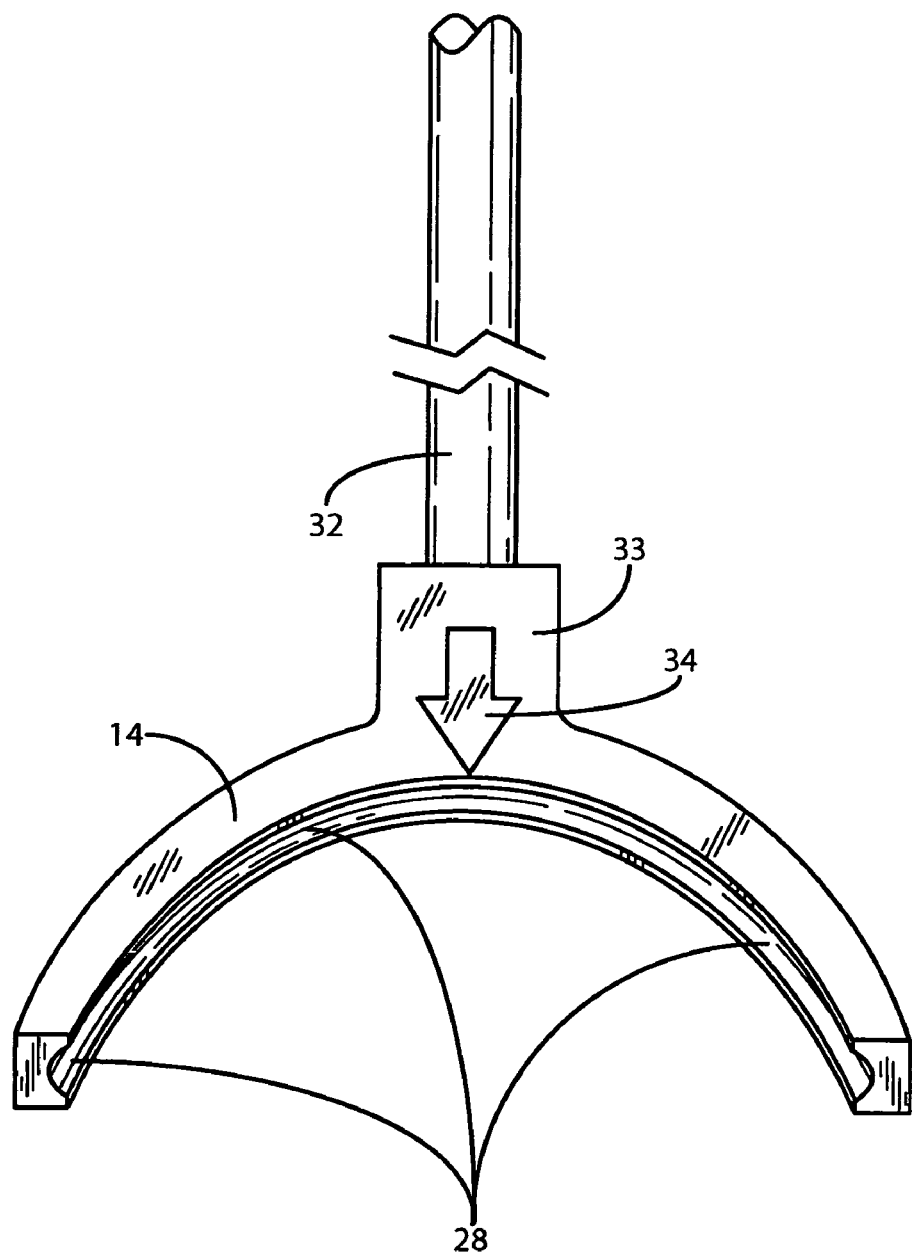
FIG. 4 shows a perspective view of the yoke of the cricoid pressure device.

Disclosed in FIG. 4, are the yoke 14 and rod 32 as they would appear if removed from the present invention. The yoke 14 is generally an arcuate portion of material and includes a rectangular connecting portion 33 that is joined at the peak of the outer surface of the arcuate portion. The interior surface of the yoke 14 has a concaved arcuate front surface 28 to conform to the neck of the patient, proximate to the cricoid cartilage. At the midpoint of the yoke 14 is a locator member 34. The locator 34 is placed adjacent to the patient's crico-thyroid membrane thereby aligning the concaved arcuate front surface 28 to the patient's cricoid cartilage. The locator 34 is used to assist the healthcare provider in aligning the yoke 14 on the patient's neck. This alignment helps to ensure the accurate placement of the device 10 on the cricoid cartilage of the patient. The locator 34 may include an alignment marking, a probe extending from yoke 14 or a highly focused light beam for example.

A rod 32 is joined to the connecting portion 33 of the yoke 14. This rod 32 is supported within housing 12 such that when pressure is applied to the yoke 28 the rod will be urged into the housing 12.

Figure 5:
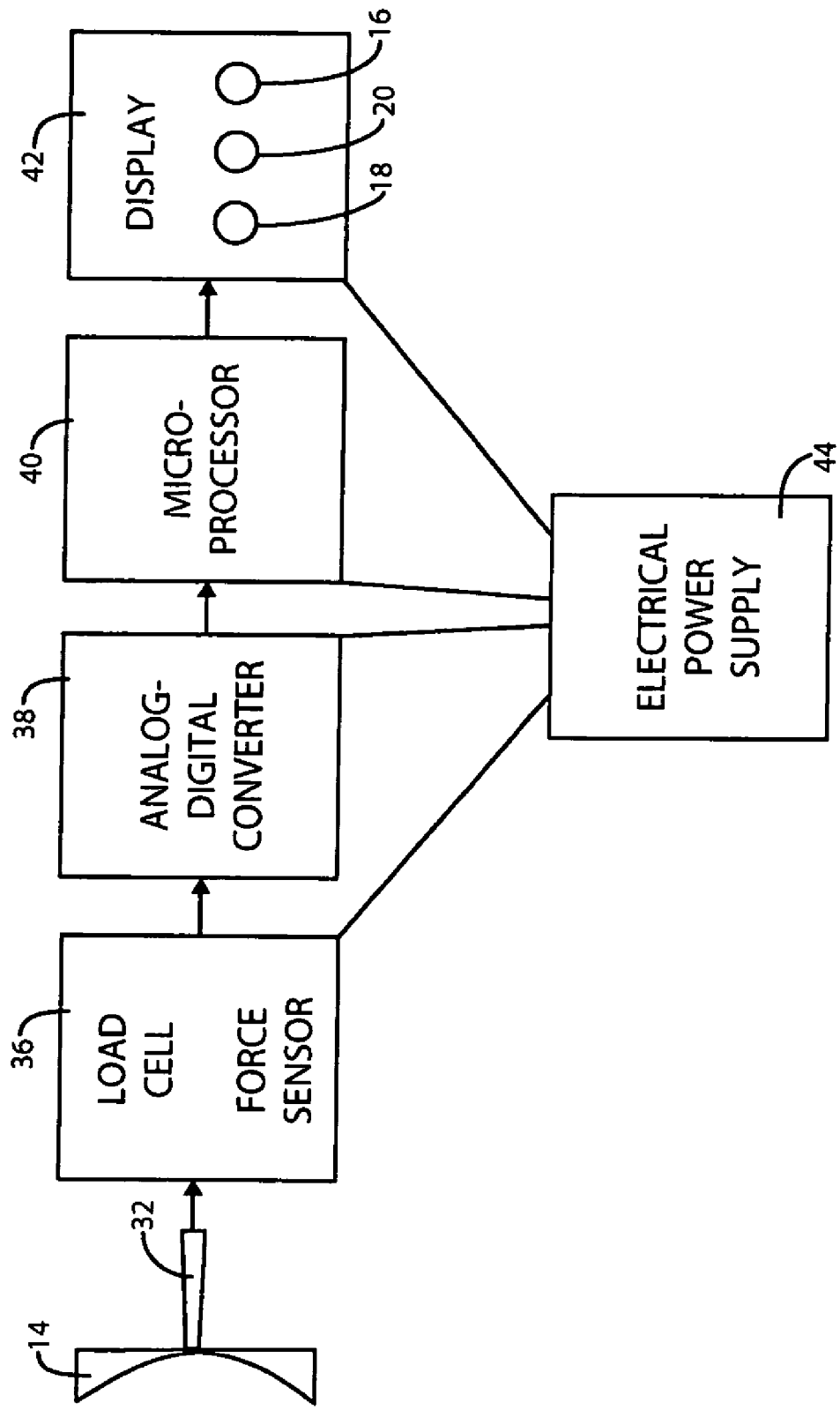
FIG. 5 is a schematic view of a means for generating a signal proportional to the amount of force applied to the cricoid by the yoke of the present invention.

FIG. 5 discloses a schematic diagram of a means for generating a signal proportional to the amount of force applied to the cricoid by the yoke of the present invention. Generally, when pressure is applied to the center of yoke 14, the rod 32 activates a force sensor or load cell 36, which determines when the healthcare provider has applied pressure within certain ranges to the cricoid cartilage of the patient. The force sensor may comprise a piezoresistive load cell.

The load cell 36 is electrically coupled to an analog-digital converter (ADC) 38. When forces are applied to load cell 36 these forces are passed on to the ADC 38. A digital signal is sent from the ADC 38 to a microprocessor 40 where the signal is compared to a preprogrammed threshold to trigger indicators 16, 18, and 20 of a display 42. If no pressure is applied to the yoke 14, then there is no digital signal and the indicators 16, 18, and 20 are off. During operation of the device power is supplied to each the load cell 36, the ADC 38, the microprocessor 40, and display 42 by an electrical power supply 44. This power supply is preferably a battery within the housing 12 of the device, however, other external or internal power sources may be used.

If the electrical power supply is sufficient and more than 0.5 N of force is applied to the yoke, indicators 16, 18 and 20 will activate sequentially. When force in the range of 0.5 N and 20±0.5 N is applied to the yoke 14, the microprocessor 40 will activate indicator 18 displaying a constant yellow LED light. When force is subsequently increased to a range between 20±0.5 N to 30±0.5 N indicator 18 is deactivated and indicator 20 will provide a predetermined intermittent signal. When force to yoke 14 is increased to a range between 30±0.5 N to an end range of 40±0.5 N indicator 20 will display a constant signal. If force greater than 41±0.5 N is applied indicator 20 will deactivate and indicator 16 display a constant signal.

While indicators 16, 18, and 20 are preferably different colored LED's, they alternatively could provide either an audio, or tactile indication that a specified amount of pressure being applied. Visually, the indicators could be red, yellow and green LED's which indicate the amount of pressure that is being applied. Alternatively, the indicator could be an LED seven segment display, which digitally indicates numerically the amount of pressure that is applied. Audibly, the indicators could offer a varying tone to indicate when pressure is within certain range. Tactilely, the indicators could set off a series of vibrations, which also indicate when a certain amount of pressure has been achieved. In addition, any combination of these visual, auditory, or tactile indicators could be used.

Where the indicators are green, red, and yellow LEDs, indicators 16, 18, and 20 are placed on the outer side of the housing, as shown in FIG. 1.

The foregoing description of the preferred embodiment is provided to meet the disclosure requirements of the patent laws. It is not intended to be limiting. The scope of the invention is defined exclusively by the following claims.

What is claimed is:

1. An instrument for indicating a force being applied to the cricoid cartilage of a patient, which comprises:
   a) a housing member adapted to allow the instrument to be grasped in a single hand of a user, the housing member including a base portion with finger grip recesses on an anterior surface and a posterior arcuate surface with a concave recess adapted for engagement with a user's thenar eminence when the base portion is being grasped;
   b) an arcuate yoke affixed to a rod, the rod being slidably supported by the housing member and said yoke shaped and dimensioned to engage the cricoid cartilage of the patient;
   c) means in the housing engaged by the rod for generating an electrical signal proportional to an amount of force applied by the user to the patient's cricoid cartilage through the yoke; and
   d) means on the housing responsive to the signal for displaying the amount of force applied to the patient's cricoid cartilage.

2. The instrument as in claim 1 wherein the means in the housing for generating a signal comprises:
   a) a force sensor positioned to be acted upon by the rod for producing an analog signal proportional to the force being applied to the cricoid membrane;
   b) an analog-to-digital converter coupled to the force sensor to receive the analog signal for producing digital values indicative of an instantaneous amplitude of the analog signal;
   c) a microprocessor coupled to the analog-to-digital converter to receive the digital values and programmed to compare said values to pre-established thresholds; and
   d) said means for displaying providing an indication of a result of the comparison.

3. The instrument as in claim 2 wherein the means in the housing for generating a signal proportional to an amount of force applied by the user to the patient's cricoid cartilage further includes an electrical power supply connected in circuit with the force sensor, the analog-to-digital converter, the microprocessor, and the means for displaying.

4. The instrument as in claim 3 where the electrical power supply comprises a battery.

5. The instrument as in claim 1 wherein the yoke has a locator for targeting the crico-thyroid membrane.

6. The instrument as in claim 5 where the locator for targeting the crico-thyroid membrane comprises a probe extending from a top surface of the yoke.

7. The instrument as in claim 2 where the force sensor comprises a load cell.

8. The instrument as in claim 7 wherein the load cell comprises a piezoresistive element.

9. The instrument as in claim 1 wherein the means for displaying comprises a series of LED lights.

10. The instrument as in claim 1 wherein the means for displaying the amount of force is configured to constantly actuate a first indicator when the force is in a range between 0.5N and 20±0.5N, a second indicator is intermittently actuated when the force is between 20±0.5N and 30±0.5N, the second indicator is constantly actuated when the force is between 30±0.5N and 40±0.5N, and a third indicator is actuated when the force is equal to or exceeds 41±0.5N.

11. The instrument as in claim 10 where the first, second and third indicators are LED lights.

12. The instrument as in claim 10 where the first, second, and third indicators are each an audible signal of a different tone pattern.

13. The instrument as in claim 10 where the first, second, and third indicators provide a different tactile vibration in the housing.

14. An instrument for indicating a force being applied to the cricoid cartilage of a subject during administration of cricoid pressure comprising:
   a) a housing member adapted to be grasped in a single hand of the user between a thumb and forefinger, the housing member including a base portion with finger grip recesses on an anterior surface and a posterior arcuate surface with a concave recess adapted for engagement with a user's thenar eminence when the base portion is being grasped and containing a force sensor for producing an electrical signal proportional to a force applied thereto, an analog-to-digital converter coupled to the force sensor, a microprocessor coupled to the analog-to-digital converter, a display and an electrical energy supply connected in circuit with the force sensor, the analog-to-digital converter, the microprocessor and the display;
   b) a yoke having a head portion with an arcuate contour shaped and dimensioned to interface with a patient's cricoid cartilage, said yoke having a generally rigid stem portion affixed to the head and projecting from one end of said housing and reciprocally slidable within the housing, the stem being operatively coupled to the force sensor for developing said electrical signal, and the analog-to-digital converter producing digital values corresponding to said electrical signal; and
   c) the microprocessor being programmed to compare the digital values to pre-established threshold values and coupled to the display to provide an indication of a result of the comparison.

15. The instrument as in claim 14 wherein the force sensor comprises a piezoresistive load cell.

16. The instrument as in claim 14 wherein the electrical energy supply comprises a battery.

17. The instrument as in claim 14 wherein the yoke has a locator member for locating the crico-thyroid membrane positioned at a midpoint of a top surface of the yoke where the locator is oriented perpendicular to the arcuate contour of the head of the yoke.

18. The instrument as in claim 14 wherein the display comprises a series of LED lights.

19. The instrument as in claim 18 wherein the indication of the result of the comparison of the digital values to pre-established threshold values;
   a) activates a first LED light when the force being applied is in a range between about 0.5N to about 20±0.5N, where the first LED light is in a constant illumination mode;
   b) when the force being applied is in a range between about 20±0.5N to about 30±0.5N the first LED light deactivates and a second LED activates where the second LED light is in a blinking mode;
   c) when the force being applied is in a range between about 30±0.5N to about 40±0.5N the second LED switches from a blinking mode to a constant illumination mode; and
   d) when the force being applied is in a range equal to or exceeding about 41±0.5N the second LED light deactivates and a third LED activates where the third LED light is in a constant illumination mode.

20. The instrument as in claim 17 where the display indicates the force being applied by giving off an audible signal.

21. The instrument in claim 17 where the display indicates the force being applied by vibrating at varying frequencies in the hand of the user.

* * * * *